United States Patent [19]
deVial

[11] 3,965,920
[45] June 29, 1976

[54] INSTALLATIONS FOR MONITORING OIL CONTENT
[75] Inventor: Raymond Michael deVial, Beckenham, England
[73] Assignee: Bailey Meters & Controls Ltd., Croydon, England
[22] Filed: Oct. 3, 1974
[21] Appl. No.: 511,748

[30] Foreign Application Priority Data
Oct. 3, 1973 United Kingdom............... 46274/73

[52] U.S. Cl................................. 137/115; 116/26; 116/65; 137/551; 250/365; 356/70
[51] Int. Cl.² ...................... G05D 7/06; F16K 37/00
[58] Field of Search ............. 340/236, 240; 116/26, 116/65; 137/115, 551; 250/365; 356/70

[56] References Cited
UNITED STATES PATENTS
3,581,085   5/1971   Barrett............................ 250/365 X
3,842,270   10/1974   Gregory et al.................. 250/365 X Primary Examiner—John W. Caldwell
Assistant Examiner—Daniel Myer
Attorney, Agent, or Firm—Kemon, Palmer & Estabrook

[57] ABSTRACT

An apparatus for detecting the presence in a liquid of material that emits fluorescent radiation when stimulated by ultraviolet radiation. A chamber having an inlet and an outlet for passing a stream of liquid therethrough. A source of ultraviolet radiation associated with said chamber with means for energizing same whereby said radiation may pass to said stream and a receiver arranged to receive fluorescent radiation emitted by such a stream.

4 Claims, 4 Drawing Figures

INSTALLATIONS FOR MONITORING OIL CONTENT

This invention relates to installations for monitoring oil content in a stream of water, and, more particularly, in a discharge of water ballast from cargo tanks of an oil tanker.

An installation for monitoring the oil content in a stream of water according to the present invention includes a sampling connection connected to receive a flow of water from the stream of water, an emulsifier connected to receive a fraction of the flow of water from the sampling connection and discharge the fraction, after thorough mixing, to a plurality of downwardly discharging orifices having co-planar axes of discharge in a sampling chamber, a beam of ultraviolet radiation of wavelength in the range 200 to 400 n.m. (wherein n.m. is the abbreviation for nanometre that is ten to the power of minus nine metres) arranged to be incident upon jets discharged from the orifices, a photo-electric cell arranged to receive fluorescent radiation emitted from the jets at wavelengths greater than 400 n.m. and an alarm circuit arranged, upon the photo-electric cell receiving radiation greater than a predetermined value, to energise a pneumatically operated alarm system by venting a pneumatic pilot pressure line.

The invention will now be described, by way of example, with reference to the accompanying partly diagrammatic drawings, in which.

The installation is utilised in connection with what is known as the "load on top" system of operation of an oil tanker vessel (not shown) in which water ballast is carried in the oil cargo tanks of the vessel and is discharged therefrom through an overboard discharge line 2 at sea during tank cleaning operations. For commercially efficient operation of such a system it is necessary to ensure discharge of all of the water from the tanks, but pollution by discharge of oil overlying the water must be avoided. To this end the discharge is continuously sampled and the sample monitored to determine the oil content by means of the fluorescence trace detector apparatus.

Figure 1A:
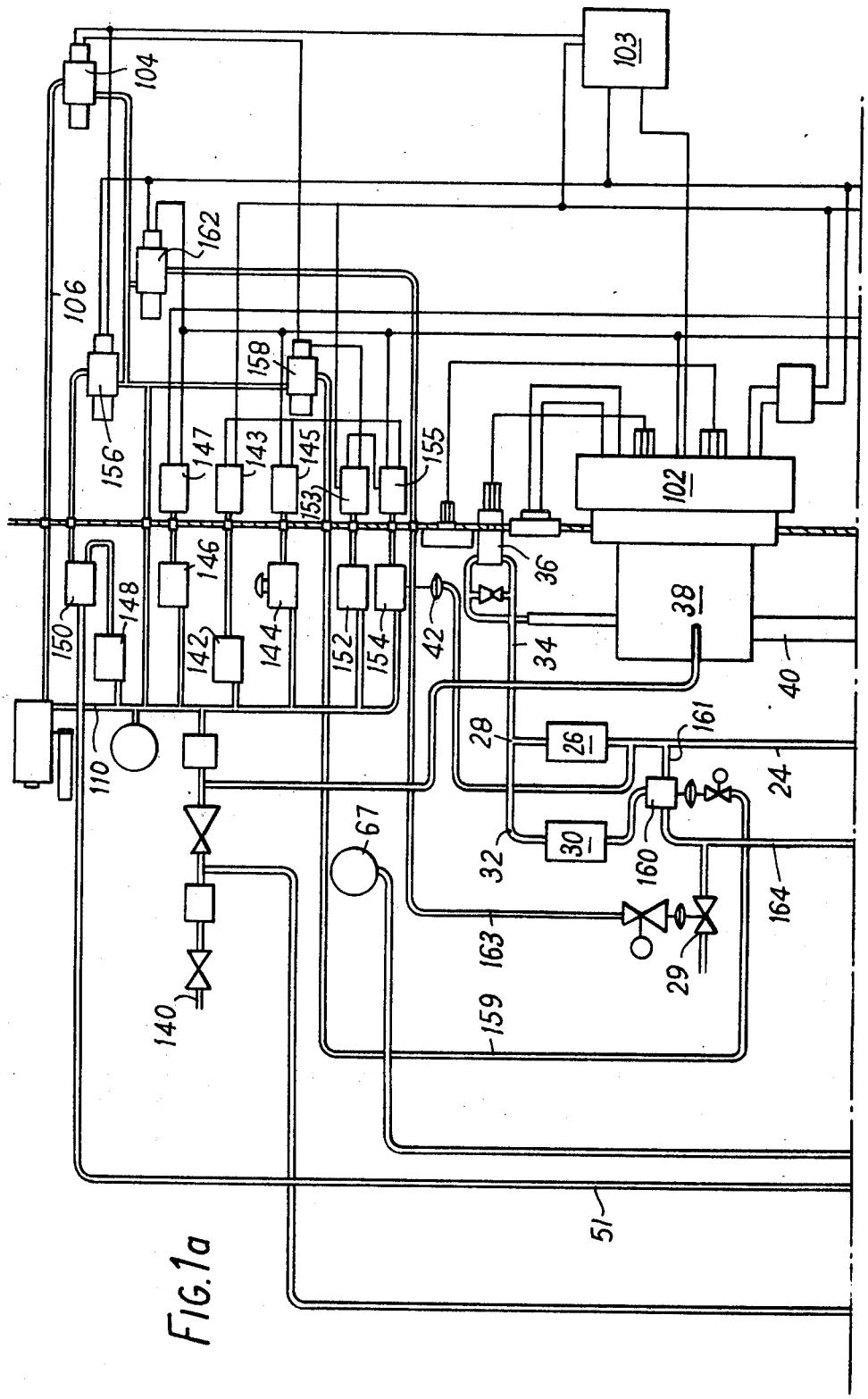
FIG. 1a is a schematic representation of a portion of the installation.
Figure 1B:
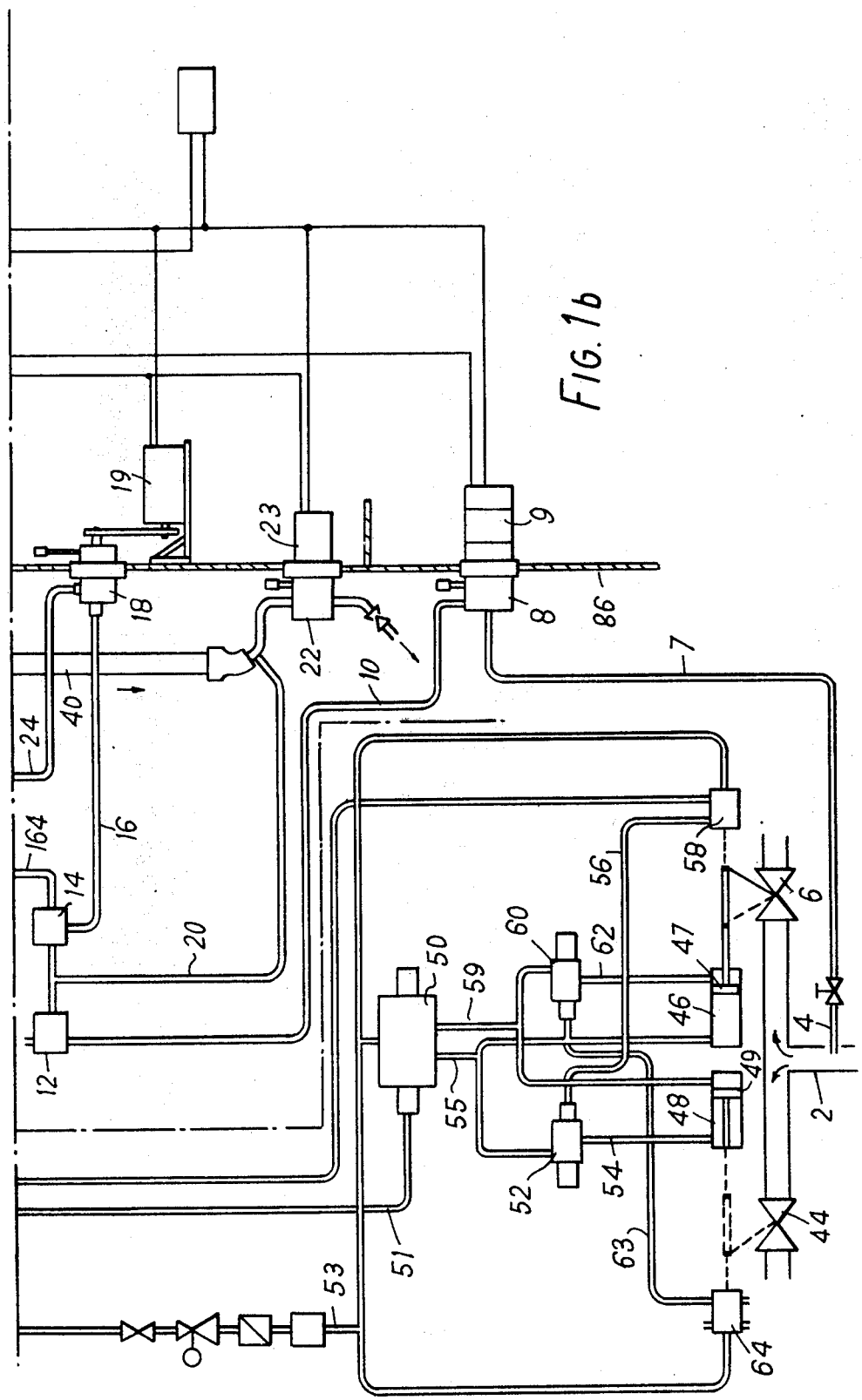
FIG. 1b is a schematic representation of another portion of the installation.

As indicated in FIG. 1b connection 4 is made to the overboard discharge line 2 just inboard of an overboard discharge sea valve 6 and leads through a line 7 to a sample lift pump 8 driven by a motor 9 supplying a continuous flow to a line 10 leading to a first selector valve 12. A fraction (approximately a quarter) of the stream is passed through a second selector valve 14 through a line 16 and through an emulsifier 18 driven by a motor 19 to reduce the size of oil particles throughout the stream, the remainder flowing through a line 20 to a drain pump 22 driven by a motor 23 discharging to a slop tank (not shown).

The emulsifier discharges through a line 24 and flow control valve 26, FIG. 1a, to a junction 28 supplied with clean sea water through a supply valve 29, a flow control valve 30 and line 32. The discharge from the emulsifier is diluted with the sea water at the junction 28 at a volume ratio of three parts sea water to one part discharge. From the junction 28 the mixed stream is discharged through a line 34 and saturation monitoring device 36 to a sampling chamber 38 and is discharged as three, free falling, jets 39 (FIG. 2) to a drain connection 40 connected to the drain pump 22.

A pressure sensor 42 is connected into the line 24 from the output side of the emulsifier 18 to produce an alarm signal should the output pressure from the emulsifier drop below a predetermined value, indicating that the supply of liquid to the emulsifier is impeded, with the danger that the instrument would give a zero reading and the emulsifier would run dry. As described later, the alarm signal originated at the pressure sensor 42, upon the emulsifier output pressure falling below the predetermined value, is arranged to effect de-energisation of the emulsifier motor 19, drain pump motor 23 and sample lift pump motor 9, together with closure of the diluting sea water valve 29 which originates visible and audible alarm signals and initiates opening of a slop tank valve 44 followed by the closing of the overboard discharge sea valve 6. Alternatively, closure of the sea discharge valve is initiated manually by the operator in response to the alarm signals.

The sea discharge valve operates in conjunction with the slop tank valve 44 such that before one closes the other is fully opened, by interlinking pneumatic actuators 46, 48 of the valves. Actuation is effected by a single pilot, spring biassed, five port valve 50. Upon applying pilot pressure through line 51 to the five port valve, the main actuating air supply in line 53 is applied through line 55 both to the front face of the sea valve actuating piston - to move the sea valve to the open position - and to a single pilot, spring-biassed three port interlock valve 52 in the slop tank valve air line 54, pilot pressure for which is supplied through a line 56 from a spring-biassed, three port valve 58 actuated by the sea valve actuator piston rod such that when the sea valve is fully open pilot pressure is supplied to the slop tank three port interlock valve 52 which moves to supply the main actuating air to the rear face of the slop tank valve actuator piston 49 to move the slop tank valve 44 to the closed position. Upon loss of pilot pressure to the five port valve 50, arising from an alarm indication or equipment failure, the front face of the piston of the sea valve actuator piston 47 and the rear face of the slop tank valve actuator piston 49 are connected to exhaust through line 55. At the same time, the main actuating air supply is applied through the five port valve 50 and line 59 to the front face of the slop tank valve actuator piston 49 - to move the slop tank valve 44 to the open position - and to a single pilot spring biassed, three port interlock valve 60 in the sea valve actuating air line, 62, pilot pressure for which is supplied through a spring biassed, three port valve 64 actuated by the slop tank valve actuator piston rod such that when the slop tank valve 44 is fully open pilot pressure is supplied through line 63 to the sea valve three port interlock valve 60 which moves to supply the main actuating air to the rear face of the sea valve actuating piston 47 to move the sea valve 6 to the closed position. From the foregoing it will be understood that the function of the interlock valves is to ensure that upon initiating changeover of discharge through the sea and slop tank valves 6, 44 the valve that was closed is moved to the fully open position before the other valve is moved to the closed position to avoid damage to the main discharge pump.

The three port valve 58 which is actuated as the sea valve moves from and to the fully closed position produces a pneumatic signal at an indicator 67 indicating the position of the sea valve 6.

The pneumatic controls on the hazardous side of a gas-tight panel 86 are linked through pneumatic lines with electrical controls on the safe side of the bulkhead. Actuating air is supplied through a line 140 and 110 to:

an emulsifier isolator pneumatic switch 142, supplying actuating air to an electrical switch 143;

an emulsifier start-up pneumatic switch 144, supplying actuating air to an electrical switch 145;

a sample selector pneumatic switch 146, supplying actuating air to an electrical switch 147;

a sea valve actuator manually operated pneumatic switch 148, supplying air to a control mode selector pneumatic switch 150 in turn supplying air to the pilot pressure line 51;

a range selector pneumatic switch 152, supplying actuating air to an electrical switch 153;

a pneumatic switch 154 connected to the pressure sensor 42 and supplying actuating air to an electrical switch 155;

a solenoid actuated pneumatic switch 156 (positioned on the safe side of the bulk head), also supplying air to the control mode selector switch 150;

a solenoid actuated pneumatic switch 158 (positioned on the safe side of the panel), supplying actuating air through a line 159 to a three way range selector valve 160 in the clean sea water supply line, a solenoid actuated pneumatic switch 162 (positioned on the safe side of the panel), supplying actuating air through a line 163 to the clean sea water supply valve 29, and the solenoid relay 104.

Figure 2:
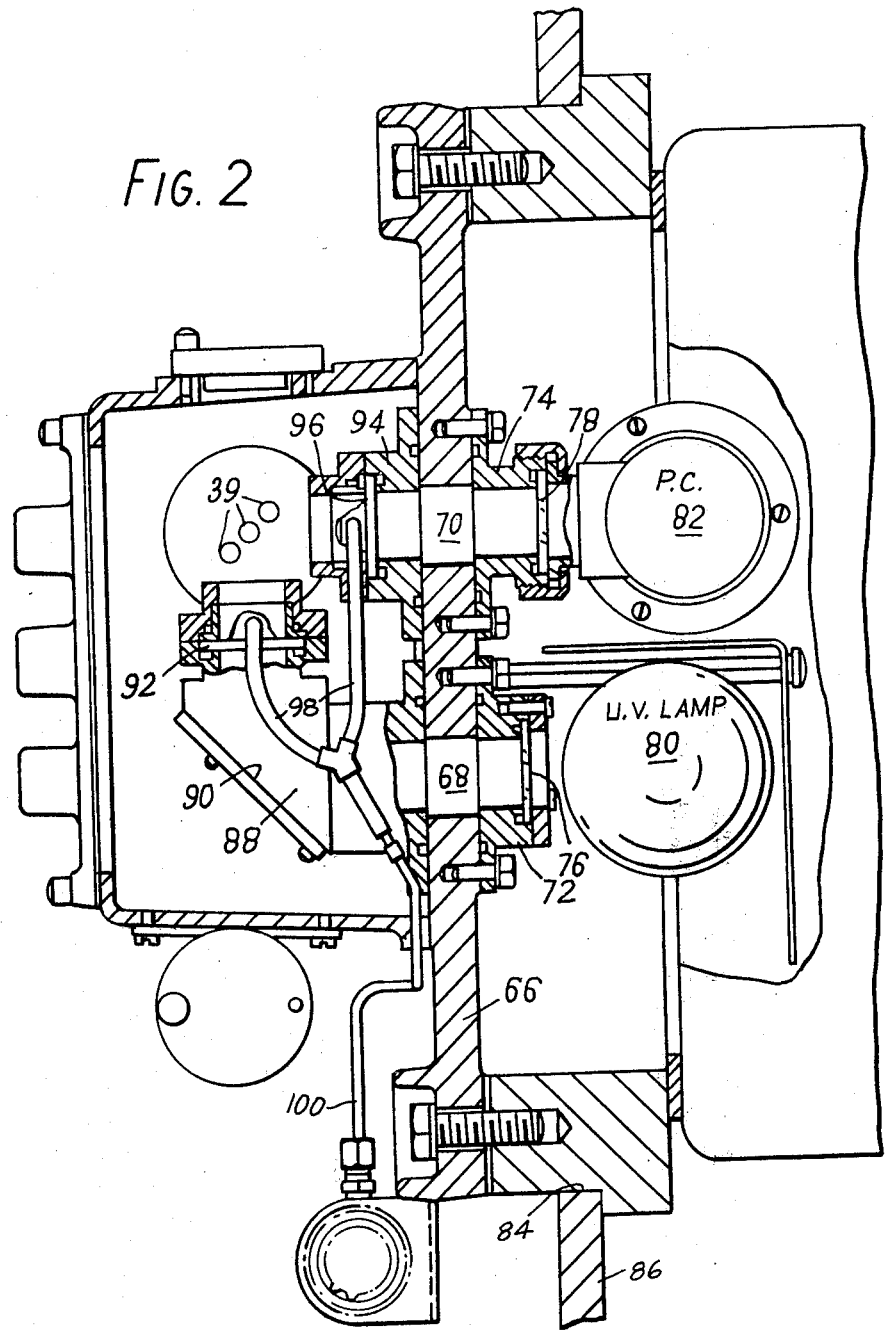
FIG. 2 is a cross-sectional plan view of a sampling chamber forming part of the installation.

Referring to FIG. 2, the sampling chamber 38 includes a frontplate 66 provided with a pair of ports 68, 70 at the same level for the beam of ultra-violet light. Short ducts 72, 74 provided with windows 76, 78 are sealed in register with an ultraviolet lamp 80 and a photocell 82. The frontplate 66 is secured in register with an aperture 84 in the gas-tight panel 86 such that all of the electrical circuitry is positioned to the safe side of the panel and is separated from the sample and the discharge lines 7 and 40, shown in FIG. 16, which are situated on the hazardous side of the panel. An elbow duct 88 is positioned internally of the chamber in register with the port 68 adjacent the ultraviolet lamp 80 and is provided with a mirror 90 at the elbow to reflect light from the ultra-violet lamp through 90° and with a window 92 at the end remote from the port. A short straight duct 94 is positioned in register with the port 70 adjacent the photocell 82 and is provided with a window 96. Streams of oil free, filtered air (from tubes 98 connected to an air supply duct 100) are directed against the faces of the windows 92, 96 open to the chamber to reduce condensation of water vapour on the windows. The intersection of the axes of the elbow duct and short straight duct within the chamber is arranged to lie on the central axis of the centre of the three free-falling jets 39, the axes of the jets lying in a plane at 45° to the axes of the short straight duct 94 and the portion of the elbow duct 88 adjacent the jets.

The ultra-violet lamp 80 is a mercury arc vapour lamp provided with a dark blue filter glass envelope to attenuate wavelengths below 330 nm harmful to the human eye and wavelengths above 400 nm, which is shorter than the wavelengths of the fluorescence arising from the contaminants, to avoid spurious readings.

The photo-cell 82 is a sensitive nine stage photomultiplier housed in a light tight container mounted on the duct 74 on the front plate. An ultra-violet blocking filter (not shown) is positioned between the window 76 in the duct and the photo-cell to attenuate any ultra-violet light that might be reflected by the jets.

Output current from the photo-cell is fed to a variable gain amplifier contained in a casing 102 FIG. 1a.

Supply voltage to the photo-cell is adjustable and provides means for compensating for variations in lamp and photo-cell characteristics. A bias control is also provided to permit suppression of small finite signals from clean sea water should a zero-based scale be required.

Figure 3:
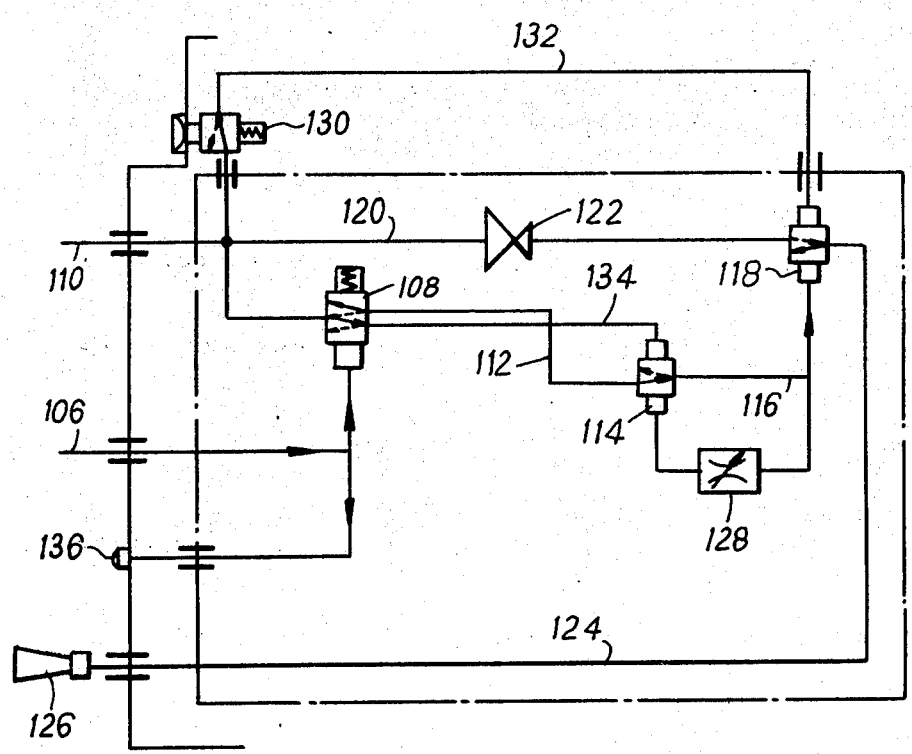
FIG. 3 is a schematic representation of an alarm circuit forming part of the installation.

The output signal from the photo-cell amplifier circuit opposes a pre-set signal generated in accordance with a predetermined alarm oil in water concentration figure such that when the two signals become equal an alarm relay opens, open circuiting an interposing alarm relay 103, so that a normally open, spring loaded, solenoid relay 104 is de-energised, activating an alarm signal. As shown in FIG. 3, de-energisation of the relay vents a pilot air pressure line 106 permitting s spring loaded five port valve 108 to move to a position in which a main air supply from a line 110 connected to the line 140 is applied, through a line 112 and a first three port double pilot operated valve 114, causing the valve 118 to move to a position in which the main air supply from an extension 120 of the line 110 leading to a pressure regulator 122 is applied through a line 124 to an alarm horn 126. The main air supply pressure through the first three port double pilot operated valve 114 is then fed back, after a short delay produced by a restrictor valve 128, as pilot pressure to the valve 114 causing it to move to an exhaust position to exhaust the pilot pressure line 116 to the second three port valve 118.

Partial re-setting of the pneumatic circuit and silencing of the alarm horn is effected by applying the main air supply pressure, through a spring loaded push bottom valve 130 normally connected to exhaust, as pilot pressure through a line 132 to the other pilot connection of the second three way valve 118, causing the valve 118 to move to disconnect the alarm horn 126 from the air supply line 120.

Upon restoration of the pilot pressure signal in the line 106, the pilot pressure moves the five port valve 108 to disconnect the main air supply line 110 from the line 112 to the first three port valve 114 and to connect the main air supply line 110 as pilot pressure through a line 134 to the other pilot connection of the valve 114 causing it to return to a ready position (as drawn) with the pilot pressure line 116 to the second three port valve 118 connected through the first three port valve 114 to exhaust through the line 112 and the five port valve 108. A visual indicator 136 is provided in the pilot air pressure line 106 indicating the existence of pilot air pressure in the line.

The saturation monitoring device 36, FIG. 1a, serves to monitor the opacity of the sample being delivered to the sampling chamber. When the concentration of oil in the water exceeds about 40,000 parts per million there is a danger that the fluorescent effect will be obscured. The saturation monitor which is not shown in detail, includes a bulb producing an intense beam of light which is projected through the stream, through self-cleaning windows in a duct, to fall upon a photo-detector cell. Circuitry associated with the cell is arranged to originate a signal upon the light reaching the cell from the bulb falling below a level corresponding to about 10,000 parts per million of oil in the water, the signal having the effect of holding the output signal from the fluorescence trace detector photo-cell amplifier circuit at the maximum value.

In operation of the fluorescence trace detection apparatus, the ultraviolet lamp 80, cooling air fan motor and electronic circuitry is energised some time before it is required to utilise the apparatus, to permit stabilisation of the ultraviolet lamp and photo-multiplier outputs and checking of operation. A reference standard fluorescing plate is inserted into the sample chamber in the position normally occupied by the falling jets 39 after cleaning the various windows and setting the required oil in water concentration alarm figure. The variable gain amplifier and photocell supply voltage are then adjusted in accordance with a calibration chart which takes into account the type of oil and time since last discharge, the reference standard removed and the sample chamber closed. After the signal on the instrument has settled, the ship's water ballast discharge operation is initiated and monitored. With the control mode selector switch 150 set for manual operation, the emulsifier isolator switches 142, 143 are set to the on position. The emulsifier start-up switches 144, 145 are held in the energising position until the emulsifier 18 runs steadily - a check being made that it is functioning correctly, since running in the absence of liquid is liable to damage the emulsifier and drain pump, and the control mode switch 150 set for automatic operation. The starter coil of the drain pump motor 23 is connected in parallel with the starter coil of the emulsifier motor 19 and hence the drain pump motor is energised when the emulsifier motor is energised. When the sample is taken from the ballast discharge line 2, as opposed to from a separator (not shown), the first selector valve 12 and the selector switches 146, 147 being appropriately positioned, the sample lift pump motor 9 is also similarly energised in parallel with the emulsifier motor 23. Otherwise, the sample is supplied to the installation from the separator through the first selector valve 12.

The clean sea water solenoid 162 is also connected in parallel with the starter coils of the emulsifier motor 19 and, when energised, supplies air from the main air supply line 140 to the line 163 to open the valve 29.

Under normal operating conditions, the range switches 152, 153 are set to high range and dilution of the sample with clean sea water is effected at the junction 28. However, where low concentrations of oil in the water sample are to be detected the diluting supply of clean sea water is discontinued, thereby effectively increasing the sensitivity by a factor of four. Upon switching to low range the solenoid switch 158 is de-energised and air is supplied from the main supply line 140 through the line 159 to the three way range selector valve 160 to disconnect the flow control valve 30 from the clean sea water supply and connect the valve 30 to receive flow from the emulsifier output line 24 through a connection 161. During operation in the low range mode should the output pressure from the emulsifier 18, as sensed by the pressure senser 42, fall below a predetermined value, the switches 154, 155 are changed over so that the motors 19, 23 and 9 and solenoid 158 are de-energised so that the selector valve 160 is restored to the high range position. Similarly, the arrangement prevents start-up of the installation in the low range mode.

It will be appreciated that since the sample lift pump supplies a stream far in excess of that required for discharge through the jets the sampling delay time is considerably reduced compared with an arrangement in which only the liquid required at the jets is abstracted from the overboard discharge line.

In an alternative arrangement, not shown, in order to effect calibration of the fluorescence trace detection apparatus, a metered flow of contaminating oil is injected into a stream of clean sea water and the variable gain amplifier and photocell supply voltage adjusted as appropriate so that the output of the photocell corresponds to the metered flow of the contaminating oil Injection of the oil into the clean sea water stream is effected at the inlet to the emulsifier 18. An elbow junction is positioned at the inlet to the emulsifier and is formed with a cylindrical chamber provided with an inlet connection in the cylindrical wall for the line 16 and a necked, discharge passage extending co-axially of the chamber connecting into the emulsifier inlet. An open ended fine bore tube extends co-axially of the chamber from an end wall remote from the emulsifier to the mid-portion of the discharge passage and terminates in a threaded nipple externally of the end wall for connection to a metering source of oil To effect calibration, the second selector valve 14 is set to isolate the line 16 from the first selector valve 12 and to connect the line 16 to the clean sea water supply valve 29 through a line 164. Water discharged from the line 16 to the emulsifier 18 is closed with a metered flow of oil at the elbow junction and the oil and water are thoroughly mixed in the emulsifier. The emulsified stream is passed to the flow control valve 26 and mixed with clean sea water from the flow control valve 30 before discharge to the fluorescent trace detector apparatus 38. Calibrating the apparatus in this manner enhances the accuracy of the apparatus, since the oil sample utilised for calibration may be derived from the load last carried and hence will have similar fluorescing properties as the oil in the ballast water.

I Claim:

1. An installation for monitoring the oil content in a discharge of water ballast from cargo tanks of an oil tanker including a sampling connection positioned adjacent a sea valve for the discharge and connected to receive a flow of water from the discharge, an emulsifier connected to receive a fraction of the flow of water from the sampling connection and discharge the fraction, after thorough mixing, to a plurality of downwardly discharging orifices having co-planar axes of discharge in a sampling chamber, a beam of ultraviolet radiation of wavelength in the range 200 to 400 n.m. arranged to be incident upon the jets discharged from the orifices, a photo-electric cell arranged to receive fluorescent radiation emitted from the jets at wavelength greater than 400 n.m. and an alarm circuit arranged upon the photo-electric cell receiving radiation greater than a pre-determined value, to energise a pneumatically operated alarm system by venting a pneumatic pilot pressure line connected to a pneumatic actuator for the sea valve and to a pneumatic actuator for a valve to a line to a slop tank for receiving water ballast unacceptable for discharge, such that upon loss of pilot pressure the slop tank valve is moved to an open position and the sea valve is moved subsequently to a closed position.

2. An installation as claimed in claim 1, wherein the pneumatic actuators are interlinked such that preparatory to closing one valve the other valve is moved to a fully open position.

3. An installation as claimed in claim 1, wherein the pneumatic pilot pressure line is connected to a pneumatic alarm horn circuit including pneumatic valves, which, upon loss of pilot pressure, serve to connect a main air supply to a sounding mechanism of the horn.

4. An installation as claimed in claim 3, wherein means are provided to disconnect the main air supply from the sounding mechanism, of the horn despite a continuing loss of pilot pressure.

* * * * *